United States Patent
Rana et al.

(10) Patent No.: US 7,056,656 B1
(45) Date of Patent: Jun. 6, 2006

(54) TAT-DERIVED OLIGOUREA AND ITS METHOD OF PRODUCTION AND USE IN HIGH AFFINITY AND SPECIFIC BINDING HIV-1 TAR RNA

(75) Inventors: Tariq M. Rana, Shrewsbury, MA (US); Natarajan Tamilarasu, Highland Park, NJ (US); Ikramul Huq, Edison, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/889,982

(22) PCT Filed: Jan. 25, 2000

(86) PCT No.: PCT/US00/01957

§ 371 (c)(1),
(2), (4) Date: Jan. 14, 2002

(87) PCT Pub. No.: WO00/43332

PCT Pub. Date: Jul. 27, 2000

Related U.S. Application Data

(60) Provisional application No. 60/117,099, filed on Jan. 25, 1999.

(51) Int. Cl.
*G01N 33/00* (2006.01)

(52) U.S. Cl. .................... 435/5; 424/188.1; 424/208.1; 436/108

(58) Field of Classification Search .................. 560/24, 560/158; 514/535, 563, 616, 575; 424/188.1, 424/208.1
See application file for complete search history.

(56) References Cited

U.S. PATENT DOCUMENTS

| 4,981,784 A | 1/1991 | Evans et al. .................... 435/6 |
| 5,071,773 A | 12/1991 | Evans et al. .................... 435/6 |
| 6,583,309 B1 * | 6/2003 | Rana et al. .................... 560/24 |

OTHER PUBLICATIONS

Tamilarasu, N., et al., 1999, "High affinity and specific binding of HIV-1 TAR RNA by a Tat-derived oligourea", J. Am. Chem. Soc. 121(7):1597-1598.*

Gait, M. J., and J. Karn, 1995, "Progress in anti-HIV structure-based drug design", TIBTECH 13:430-438.*

Aboul-ela, Fareed et al., The Structure of the Human Immunodeficiency Virus Type-1 TAR RNA Reveals Principles of RNA Recognition by Tat Protein, *Journal of Molecular Biology* 253(2), Oct. 20, 1995, pp. 313-332.

(Continued)

*Primary Examiner*—J S Parkin
(74) *Attorney, Agent, or Firm*—Hoffman & Baron, LLP

(57) ABSTRACT

This invention relates to the use of oligourea molecules to specifically inhibit protein-nucleic acid interactions. In particular, it provides an oligourea molecule that competes with the Tat molecule for the TAR RNA of HIV-1. Also provided is a method specifically inhibiting protein-nucleic and interactions, and kits.

13 Claims, 4 Drawing Sheets

OTHER PUBLICATIONS

Burgess, Kevin, et al., Solid Phase Syntheses of Oligoureas, *J. Am. Chem. Soc.* 119, 1997, pp. 1556-1564.

Burgess, Kevin, et al., Solid-Phase Syntheses of Unnatural Biopolymers Containing Repeating Urea Units, *Andewandte Chemie International Edition in English* 34, 1995, pp. 907-909.

Calnan, Barbara J. et al., Analysis of arginine-rich peptides from the HIV Tat protein rveals unusual feature sof RNA-protein recognition, *Genes & Development* 5, 1991, pp. 201-210.

Churcher, Mark J. et al., High Affinity Binding of TAR RNA by Human Immunodeficiency Virus Type-1 tat Protein Requires Base-pairs in the RNA Stem and Amino Acid Residues Flanking the Basic Region, *Journal of Molecular Biology* 230(1), Mar. 5, 1993, pp. 90-110.

Cullen, Bryan R., Mechanism of Action of Regulatory Proteins Encoded by Complex Retroviruses, *Microbiological Review* 56(3), Sep. 1992, 56, pp. 375-394.

Cusack, Stephen, RNA-protein complexes, *Curr. Opin. Struct. Biol.* 9(1), Feb. 1999, pp. 66-73.

Draper, David E., Themes in RNA-Protein Recognition, *J. Mol. Biol.*293(2), Oct. 22, 1999, pp. 255-270.

Garell, Joan et al.,The Helix-Loop-Helix Domain: A Common Motif for Bristles, Muscles and Sex, *Bioessays*, 13(10), 1991, pp. 493-498.

Gaynor, Richard, Cellular transcription factors involved in the regulation of HIV-1 gene expression, *AIDS* 6, 1992, pp. 347-363.

Geierstanger, Berhard H. et al., Design of a G•C-Specific DNA Minor Groove-Binding Peptide, *Science* 266, 1994, pp. 646-650.

Gottesfeld, Joel M. et al., Regulation of gene expression by small molecules, *Nature* 387, 1997, pp. 202-205.

Haile, David J., MD, Regulation of Genes of Iron Metabolism by the Iron-Response Proteins, *Am. J. Med. Sci* 318(4), Oct. 1999, pp. 230-240.

Harrison, Stephen C., A structural taxonomy of DNA-binding domains, *Nature* 353, Oct. 24, 1991, pp. 715-719.

Huq, Ikramul et al., Probing the Proximity of the Core Domain of an HIV-1 Tat Fragment in a Tat-TAR Complex by Affinity Cleaving, *Biochem.* 36, 1997, pp. 12592-12599.

Jacobs, Grant H., Determination of the base recognition positions of zinc fingers from sequence analysis, *The EMBO Journal* 11(12), 1992, pp. 4507-4517.

Jeang, Kuan-Teh et al., Effects of Integration and Replication on Transcription of the HIV-1 Long Terminal Repeat, *J. Biol. Chem.* 268(33), Nov. 25, 1993, pp. 24940-24949.

Jones, Katherine A. et al., Control of RNA Initiation and Elongation at the HIV-1 Promoter, *Annu. Rev. Biochem.* 63, 1994, pp. 717-743.

Kadesch, Tom, Helix-loop-helix proteins in the regulation of immunoglobulin gene transcription, *Immun. Today*, 13(1), 1992, pp. 31-36.

Kick, Ellen K. et al., Expedient Method for the Solid-Phase Synthesis of Aspartic Acid Protease Inhibitors Directed toward the Generation of Libraries, *J. Med. Chem.* 38, 1995, pp. 1427-1430.

Kim, Jong-Man et al., The Solid Phase Synthesis of Oligoureas, *Tetrahedron Lett.* 37(30), 1996, pp. 5305-5308.

Klug, Aaron et al., 'Zinc fingers': a novel protein motif for nucleic acid recognition, *Trends Biochem Sci.* 12, 1987, pp. 464-469.

Lamb, Peter et al., Diversity and specificity in transcriptional regulation: the benefits of heterotypic dimerization, *Trends Biochem. Sci.* 16, 1991, pp. 417-422.

Leonard, James et al., Characterization of Somatostatin Transactivating Factor-1, a Novel Homeobox Factor That Stimulates Somatostatin Expression in Pancreatic Islet Cells, *Mol. Endo.* 7, 1993, pp. 1275-1283.

Pabo, Carl O. et al., Protein-DNA Recognition, *Annu. Rev. Biochem.* 53, 1984, pp. 293-321.

Puglisi, Joseph D. et al., Conformation of the TAR RNA-Arginine Complex by NMR Spectroscopy, *Science* 257, 1992, pp. 257, 76-80.

Sambrook et al., *Molecular Cloning*, Cold Spring Harbor Laboratory, 1989.

Scott, Matthew P. et al., The structure and function of the homeodomain, *Biochem, Biophys. Acta.* 989, 1989, pp. 25-48.

Tinoco, I., Jr. et al., RNA Folding, *Nucl. Acids & Mol. Biol.* 4, 1990, pp. 205-226.

Tsay, H.-J. et al., CTF4, a chicken transcription factor of the helix-loop-helix class A family, *NAR* 20(10), 1992, p. 1805.

Wang, Xilu et al., HIV-1 TAR RNA Recognition by an Unnatural Biopolymer, *J. Am. Chem. Soc.* 119, 1997, pp. 6444-6445.

Wang, Zhuying et al., Chemical Conversion of a trans-Activation Responsive RNA-Binding Fragment of HIV-1 Tat Protein into a Site- Specific Cross-Linking Agent, *J. Am. Chem. Soc.* 117, 1995, pp. 5438-5444.

Wang, Zhuying et al., Protein Orientation in the Tat-RAT Complex Determined by Psoralen Photocross-linking, *J. Biol. Chem.* 271(29), 1996, pp. 16995-16998.

Wang, Zhuying et al., RNA Conformation in the Tat-TAR Complex Determined by Site-Specific Photo-Cross-Linking, *J. Biochem* 35, 1996, pp. 6491-6499.

Weeks, Kevin M. et al., RNA Recognition by Tat-Derived Peptides: Interaction in the Major Groove?, *Cell* 66, 1991, pp. 577-588.

White, Sarah et al., Recognition of the four Watson-Crick base pairs in the DNA minor groove by synthetic ligands, *Nature* 391, 1998, pp. 468-471.

Ausubel, Frederick M. et al., *Current Protocols in Molecular Biology*, John Wiley & Sons, Inc., Apr. 1993.

Block, Nancy E. et al., Expression of MRF4, a Myogenic Helix-Loop-Helix Protein, Produces Multiple Changes in the Myogenic Program of BC3H-1 Cells, *Mol. and Cell. Biol.* 12(6), Jun. 1992, pp. 2482-2492.

Conaway, Ronald C. et al., *Transcription: Mechanisms and Regulation*, Raven Press Series on Molecular and Cellular Biology, vol. 3, Raven Press, Lt., New York, NY, 1994.

Jacobs, Grant et al., Zinc Finger Gene Database, *The New Biologist* 2(6), Jun. 1990, pp. 583-584.

Wright, Woodring, E., Muscle basic helix-loop-helix proteins and the regulation of myogenesis, *Current Opinion in Genetics and Development* 2(2), Current Biology Ltd., Apr. 1992, pp.: 243-248.

* cited by examiner

⁴⁸Gly-Arg-Lys-Lys-Arg-Arg-Gln-Arg-Arg-Arg⁵⁷

Wild-type TAR

US 7,056,656 B1

TAT-DERIVED OLIGOUREA AND ITS METHOD OF PRODUCTION AND USE IN HIGH AFFINITY AND SPECIFIC BINDING HIV-1 TAR RNA

This application is a 35 U.S.C. §371 National Stage Application of International Application No. PCT/US00/01957, filed Jan. 25, 2000, which claims the benefit of U.S. Provisional Application No. 60/117,099, filed Jan. 25, 1999, all of which are herein incorporated by reference.

This work was supported in part by the National Institutes of Health Grants Al 34785 and Al 01369, TW 00702. Tariq M. Rana is a recipient of Research Career Development Award from NIH.

FIELD OF THE INVENTION

This invention relates to a synthesized oligourea containing the basic-arginine rich region of Tat, the method of production of this oligourea and the use thereof. In particular, this invention relates to the design of drugs comprising the oligourea backbone of the invention, further comprising amino acid side chains. Similarly, the DNA-binding oligourea of the invention can also be synthesized to control biological processes involving DNA-protein interactions

BACKGROUND OF THE INVENTION

Various scientific and scholarly articles are referred to in brackets and footnotes throughout the specification. These articles are incorporated by reference herein to describe the state of the art to which this invention pertains. Full citations of the references appear at the end of the specification.

Protein-nucleic acid interactions are involved in many cellular functions such as transcription, RNA splicing, and translation. Small peptides with unnatural backbones that can bind with high affinity to a specific sequence or structure of nucleic acids and interfere with protein-nucleic acid interactions would provide useful tools in molecular biology and medicine. Recently, minor-groove-binding polyamide ligands have been designed for sequence-specific recognition of DNA.[1] In contrast to DNA, RNA molecules can fold into extensive structures containing regions of double-stranded duplex, hairpins, internal loops, bulged bases and pseudo-knotted structures.[2] The complexity of RNA structure makes it difficult to design ligands for sequence-specific RNA-recognition. Three-dimensional structures of RNA create binding sites for specific interactions with proteins.

One example of such interactions is the mechanism of trans-activation of human immunodeficiency virus type 1 (HIV-1) gene expression that requires the interaction of Tat protein with the trans-activation responsive region (TAR) RNA, a 59-base stem-loop structure located at the 5'-end of all nascent HIV-1 transcripts.[3] Replication of human immunodeficiency virus type 1 (HIV-1) requires specific interactions of Tat protein with the TAR RNA. Inhibition of Tat-TAR interactions is a potential approach for anti-HIV therapeutics. Since structural information is now available for TAR RNA and TAR-Tat peptide complexes from NMR[4], photocrosslinking,[5] and affinity cleaving studies,[6] it is possible to design small molecules to interfere with Tat-TAR function. We have recently begun to examine TAR RNA recognition by unnatural biopolymers.[7]

OBJECTS OF THE INVENTION

It is an object of the invention to provide substances which have higher binding affinities for RNA than natural peptides, which are resistant to proteases and which can interact with nucleic acids in a fashion similar to natural peptides. Such substances can be used to inhibit protein-nucleic acid interactions important for cellular processes.

It is a further object of the invention to provide a substance inhibiting protein-nucleic acid interactions. In particular, it is an object of the invention to provide a substance which controls biological processes involving DNA-protein interactions, and which inhibit transcription in HIV-1 infected cells. Such a substance leads to the design of drugs based on the substance.

The current invention comprises a novel synthesized oligourea containing the basic-arginine rich region of Tat. The oligourea of the invention shows specific recognition of HIV-1 TAR RNA.

Other objects and advantages of the invention will become apparent to those skilled in the art from the accompanying description of the invention.

DETAILED DESCRIPTION OF THE INVENTION

The invention provides a composition and method for inhibiting the interaction of a nucleic acid and specific binding protein in vitro and in vivo. The composition is an oligourea backbone as disclosed in FIG. 1B, with amino acid side-chains substituted at the $R_1$ and $R_2$ positions. In accordance with the invention, it has been discovered that the rigid and protease insensitive oligourea backbone, when substituted with a sequence of amino acid side-chains modeled after a known nucleic acid binding domain, will mimic the nucleic acid binding domain in specificity, but with a much lower disassociation constant. This nucleic acid binding composition may be used for research into the physiological effects of nucleic acid binding proteins, assay methods for detecting nucleic acids and therapeutic methods for inhibiting protein-nucleic acid interactions that lead to disease states. Also provided, is a method for inhibiting protein-nucleic acid interactions in vitro and in vivo which entails introducing the oligourea molecules of the invention.

Figures 1A, 1B:
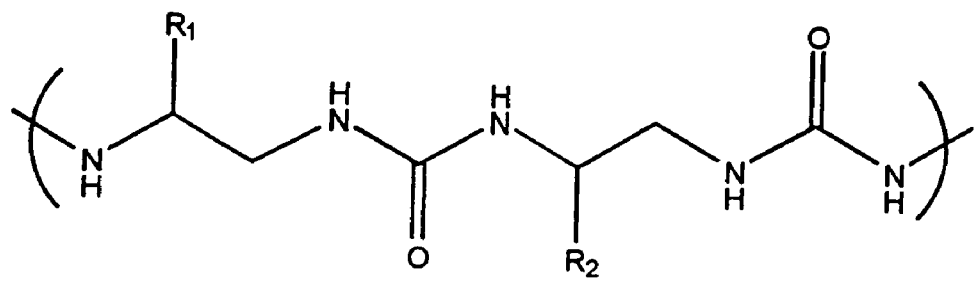
FIG. 1A: The Tat-derived peptide, amino acids 48 to 57, contains the RNA-binding domain of Tat protein (SEQ ID NO:1).
FIG. 1B: Structure of the generic oligourea backbone. Side-chains corresponding to a desired amino acid are substituted at the $R_1$ and $R_2$ positions. Sequence of Tat-derived oligourea corresponds to the side-chains of the Tat peptide shown in (A), except the addition of an L-Tyr amino acid at the carboxyl-terminus. Tat-derived oligourea was synthesized on solid support by using activated p-nitrophenyl carbamates and azides of protected amines followed by reduction with $SnCl_2$-thiophenol-triethylamine (Kim, J. M.; Bi, Y. Z.; Paikoff, S. J.; Schultz, P. G. *Tetrahedron Lett.* 1996, 37, 5305–5308; Kick, B.; Bllman, J. *J Med. Chem.* 1995, 38, 1427–1430; incorporated by reference herein). After cleavage from the resin, the oligourea was purified by HPLC on a Zorbax 300 SB-$C_8$ column (Wang, Z.; Rana, T. M. *J Am. Chem. Soc.* 1995, 117, 5438–5444; Wang, Z.; Rana, T. M. *Biochemistry* 1996, 35, 6491–6499; Wang, Z.; Wang, x.; Rana, T. M. *J Biol. Chem.* 1996, 27, 16995–16998; incorporated by reference herein). The mass of fully deprotected and purified oligourea was confirmed by ES and MALDI mass spectrometry; 1849.2 (M+H).
Figure 2A:
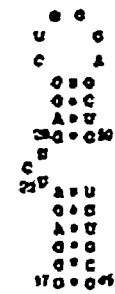
FIG. 2A: Secondary structure of wild-type TAR RNA used in this study. Wild-type TAR RNA spans the minimal sequences that are required for Tat responsiveness in vivo [14] and for in vitro binding of Tat-derived peptides.[9] Wild-type TAR contains two non-wild-type base pairs to increase transcription by T7 RNA polymerase. Mutant M0 TAR contained no bulge residue in its sequence. In mutant G26C, a base-pair in the upper stem of TAR RNA, G26-C39 was substituted by C26-G39.
Figure 2B:
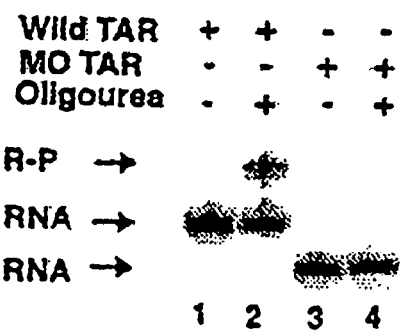
FIG. 2B: Electrophoretic mobility shift analysis for the Tat-derived oligourea binding to wild-type and trinucleotide bulge mutant (M0) TAR RNA. 5'-end labeled TAR RNAs (40 nM) were heated to 85° C. for three minutes mm and then cooled to room temperature in TK buffer (50 mM Tris-HCl pH 7.4), 20 mM KCl, 0.1% Triton X-100). The oligourea (150 nM) was added to wild-type or mutant TAR and incubated at room temperature for one hour. After adding 30% glycerol, the oligourea-RNA complexes were resolved on a non-denaturing 12% acrylamide gel and visualized by autoradiography or phosphorimaging.

The composition of the invention is composed oligourea backbone, the generic form of which is disclosed in FIG. 1B, which supports the side chains of amino acids, at the $R_1$ and $R_2$ position of FIG. 2B. When the oligourea molecule has amino acid side chains that correspond to the side chains of a nucleic acid binding protein in composition and sequence, the oligourea molecule then binds to the target nucleic acid specifically and with a very low disassociation constant. In a preferred embodiment, the oligourea molecule has a dissociation constant upon binding the target nucleic acid of less than or equal to 0.7 μM (less than or equal to 0.5 μM more preferred; less than or equal to 0.3 μM most preferred). In Example 1, the use of an oligourea molecule of the invention is illustrated which mimics the RNA-binding protein Tat. In a preferred embodiment, the oligourea molecule is comprised of amino acid side chains that mimic the Tat molecule. In a more preferred embodiment, the side-chains correspond to residues 48–57 of the Tat molecule, more preferred, SEQ ID NO:1. In a most preferred embodiment, the amino acid side-chains correspond to SEQ ID NO:1 with a L-Tyr amino acid at the carboxyl-terminus.

The composition of the invention encompasses a very diverse assortment of molecules, all with oligourea backbones and amino acid side-chains. The oligourea molecule may be any length which achieves the desired dissociation constant from the nucleic acid. In a preferred embodiment, the oligourea is 3 to 50 urea-units long (5 to 30 more preferred, 8 to 25 most preferred). The oligourea molecule may comprise amino acid side-chains that correspond to the binding region of any nucleic acid binding protein presently known or that will be discovered. Types of DNA binding proteins of interest include, but are not limited to, transcription control proteins (e.g. transcription factors, see Conaway and Conaway, 1994, *Transcription Mechanisms and Regulation*, Raven Press Series on Molecular and Cellular Biology, Vol. 3, Raven Press, Ltd., New York, N.Y.), recombination enzymes (e.g. hin recombinase), DNA modifying enzymes (e.g. restriction enzymes), structural proteins (e.g. histones and nonhistone chromatin proteins such as HMG proteins), single-stranded DNA-binding proteins (e.g. those involved in the propagation of a DNA replication fork or in the packaging of T-DNA ssDNA) and double- and single-stranded RNA-binding proteins. RNA-binding proteins are also contemplated in regard to the present invention, (see, for example, Draper D E, J Mol Biol 1999 Oct. 22; 293(2): 255–70; Haile D J, Am J Med Sci 1999 October; 318(4): 230–40; Cusack S, Curr Opin Struct Biol 1999 February; 9(1):66–73).

Transcription factors suitable for use with the present invention include, but are not limited to, homeobox proteins, zinc finger proteins, hormone receptors, helix-turn-helix proteins, helix-loop-helix proteins, basic-Zip proteins (bZip) and β-ribbon factors (see Harrison, 1991, Nature 353:715–719). Homeobox DNA-binding proteins contemplated for use with the instant invention include, but are not limited to, HOX, STF-1 (Leonard et al., 1993, Mol. Endo., 7:1275–1283; Scott et al. (1989), Biochem. Biophys. Acta, 989:25–48), Antp, Mat α-2 and INV. Zinc finger DNA-binding proteins contemplated for use with the instant invention include, but are not limited to, Zif268, GLI and XFin. For reviews of zinc-finger DNA-binding proteins see Klug and Rhodes (1987), Trends Biochem. Sci., 12:464; Jacobs and Michaels (1990), New Biol., 2:583; and Jacobs (1992), EMBO J., 11:4507–4517. Hormone receptor DNA-binding proteins contemplated for use with the instant invention include, but are not limited to, glucocorticoid receptor, thyroid hormone receptor and estrogen receptor (see, e.g., U.S. Pat. Nos. 4,981,784; 5,171,671; and 5,071,773). Helix-turn-helix DNA-binding proteins contemplated for use with the instant invention include, but are not limited to, λ-repressor, cro-repressor, 434 repressor and 434-cro (See, e.g., Pabo and Sauer, 1984, Annu. Rev. Biochem., 53:293–321). Helix-loop-helix DNA-binding proteins contemplated for use with the instant invention include, but are not limited to, MRF4 (Block et al., 1992, Mol. and Cell Biol., 12(6):2484–2492), CTF4 (Tsay et al., 1992, NAR, 20(10):2624), NSCL, PAL2 and USF (see, for review, Wright (1992), Current Opinion in Genetics and Development, 2(2):243–248; Kadesch, T. (1992), Immun. Today, 13(1):31–36; and Garell and Campuzano (1991), Bioessays, 13(10):493–498). Basic Zip DNA-binding proteins contemplated for use with the instant invention include, but are not limited to, GCN4, fos and jun (see, for review, Lamb and McKnight, 1991, Trends Biochem. Sci., 16:417–422). β-ribbon factors contemplated for use with the instant invention include, but are not limited to, Met-J, ARC, and MNT.

The oligourea composition of the invention has a diverse range of uses. Any application that requires a strong nucleic acid binding molecule may use the oligourea molecules of the invention. The oligourea molecules may be used to inhibit the native nucleic acid binding molecule by competing with the native protein molecule for the binding site on the nucleic acid. This application may be used for research purposes or for therapy purposes. In therapeutic methods, the oligourea molecules of the invention may be used to inhibit a protein-nucleic interaction that leads to a disease state. Example 1 illustrates the use of an oligourea molecule to inhibit the interaction between the Tat protein and the TAR RNA from HIV. Finally, the oligourea molecule may be used to detect the presence of the target nucleic acid molecule in any method that requires the detection and/or quantization of a specific nucleic acid.

A method to inhibit the interaction between a specific interaction between a binding protein and its target nucleic acid comprising introducing an oligourea molecule that specifically competes with the binding protein for the binding site on the target nucleic acid. In a preferred embodiment, the method is a therapeutic method for patients in need of such a treatment. This method is particularly suited as therapeutic method because of the high specificity of the inhibition provided. The therapeutic method is applicable to any disease state in which a nucleic acid-protein interaction affects the disease state. In a preferred embodiment, the patient is human. In a more preferred the patient is infected by the HIV-1 virus, and the oligourea molecule introduced comprises amino acid side chains that correspond to the Tat molecule.

The following Example sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (2000) (hereinafter "Ausubel et al.") are used.

The following example is provided to describe the invention in greater detail. It is intended to illustrate, not to limit, the invention.

EXAMPLE I

We synthesized an oligourea containing the basic-arginine rich region of Tat by solid phase synthesis methods, and tested for TAR RNA binding. This tat-derived unnatural biopolymer binds TAR RNA specifically with affinities higher than the wild-type Tat peptide. Site-specific photo-crosslinking experiments using a photoactive analog (4-thio-uracil) containing TAR RNA revealed that the unnatural biopolymer interacts with RNA in the major groove. The oligourea-RNA complexes were stable to proteolytic digestion. RNA recognition by an oligourea provides a new class of RNA-binding molecules that can be used to control cellular processes involving RNA-protein interactions in vivo.

In this report, we synthesized an oligourea containing the basic-arginine rich region of Tat by solid phase synthesis methods, and tested for TAR RNA binding. Oligoureas have backbones with hydrogen bonding groups, chiral centers, and a significant degree of conformational restriction. Introducing additional side chains at the backbone NH sites can further modify biological and physical properties of these oligomers. This tat-derived unnatural biopolymer binds specifically to TAR RNA with affinities higher than the wild-type Tat peptide. These results identify a new class of unnatural peptides for structure-specific recognition of RNA.

The promoter of HIV-1, located in the U3 region of the viral long terminal repeat (LTR), is an inducible promoter which can be stimulated by the trans-activator protein, Tat.[3] As in other lentiviruses, Tat protein is essential for trans-activation of viral gene expression.[8] A number of studies showed that Tat-derived peptides which contain the basic arginine-rich region of Tat are able to form in vitro complexes with TAR RNA.[9] We synthesized a tat-derived oligourea containing the basic-arginine rich region of Tat protein by solid phase synthesis methods (FIG. 1). Recently, two methods have been reported for solid phase synthesis of oligourea.[10,11] To synthesize Tat-derived oligourea on solid support, we used activated p-nitrophenyl carbamates and protected amines in the form of azides, which were reduced with $SnCl_2$-thiophenol-triethylamine on solid support.[11,12] After HPLC purification and characterization by mass spectrometry, the oligourea was tested for TAR RNA binding (FIG. 2). The tat-derived oligourea was able to bind TAR RNA and failed to bind a mutant TAR RNA without the bulge residues.

Equilibrium dissociation constants of the oligourea-TAR RNA complexes were measured using direct and competition electrophoretic mobility assays.[13] Dissociation constants were calculated from multiple sets of experiments which showed that the oligourea binds TAR RNA with a $K_D$ of 0.11±0.07 μM. To compare the RNA-binding affinities of the oligourea to natural peptide, we synthesized a tat-derived peptide (Tyr47 to Arg57) containing the RNA-binding domain of Tat protein (FIG. 1). Dissociation constants of the Tat peptide-RNA complexes were determined from multiple sets of experiments under the same conditions used for oligourea-TAR RNA complexes. These experiments showed that the Tat peptide (47–57) binds TAR RNA with a $K_D$ Of 0.78+0.05 μM. A relative dissociation constant ($K_{REL}$) can be determined by measuring the ratios of wild-type Tat peptide to the oligourea dissociation constants ($K_D$) for TAR RNA. Our results demonstrate that the calculated value for $K_{REL}$ was 7.09, indicating that the urea backbone structure enhanced the TAR binding affinities of the unnatural biopolymer.

Figure 2C:
FIG. 2C: Specificity of the oligourea-TAR complex formation determined by competition experiments. Oligourea-RNA complexes were formed in the presence of increasing concentrations of unlabeled wild-type or mutant TAR RNAs. Concentrations of the competitor RNAs in lanes 3, 4, 5, 6 were 50, 100, 150, and 200 nM, respectively. Lanes 1 and 2 were marker lanes showing RNA and oligoureaRNA complexes. Oligourea-RNA complexes are labeled as R—P.

Specificity of the oligourea-TAR RNA complex formation was addressed by competition experiments (FIG. 2c). Oligourea-RNA complex formation was inhibited by the addition of unlabeled wild-type TAR RNA and not by mutant TAR RNAs. Mutant TAR RNA without a trinucleotide bulge (FIG. 2c) or with one base bulge (data not shown) was not able to compete for oligourea binding to wild-type TAR RNA.

Two base-pairs immediately above the pyrimidine bulge are critical for Tat recognition.[9] To determine whether the oligourea recognizes specific base-pairs in the stem region of TAR RNA or only a trinucleotide bulge containing RNA, we synthesized a TAR mutant where the G26-C39 base pair was substituted by a C26-G39 base-pair (FIG. 2a). Competition experiments showed that this mutant TAR (G26C) did not inhibit Oligourea binding to TAR RNA (FIG. 2c). These results indicate that the tat-derived oligourea can specifically recognize TAR RNA.

Figure 3:
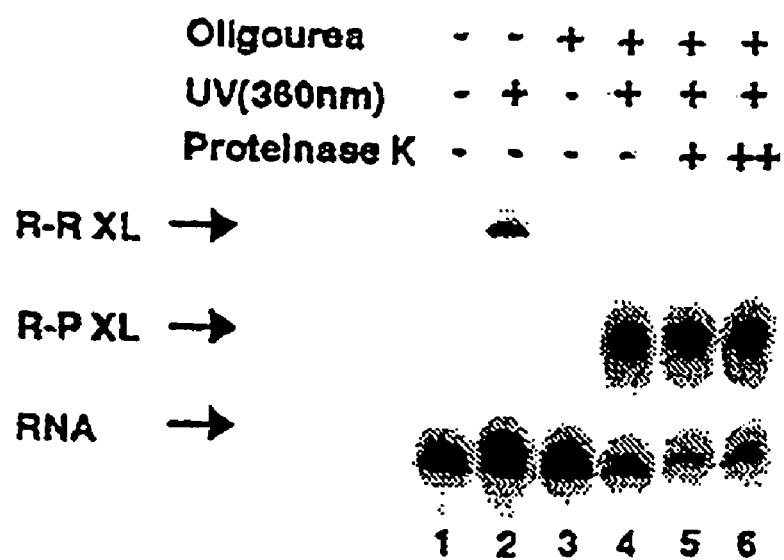
FIG. 3. Site-specific photocrosslinking reaction of TAR RNA labeled with 4-thioUracil at position 23 with the oligourea. For photochemical reactions, RNA duplex was prepared by hybridizing two strands.[5,7] Strand 1 of the duplex was 5'-end labeled with 32p Preformed RNA duplexes (40 nM) in the absence or presence of the oligourea (100 nM) were irradiated (360 um) and analyzed by denaturing gels as described earlier.[5,7] Proteinase K digestion was performed at 55° C. for fifteen minutes after LW irradiation. R—R and R—P XL indicate the RNA—RNA and RNA-oligourea crosslink, respectively.
Figure 4:
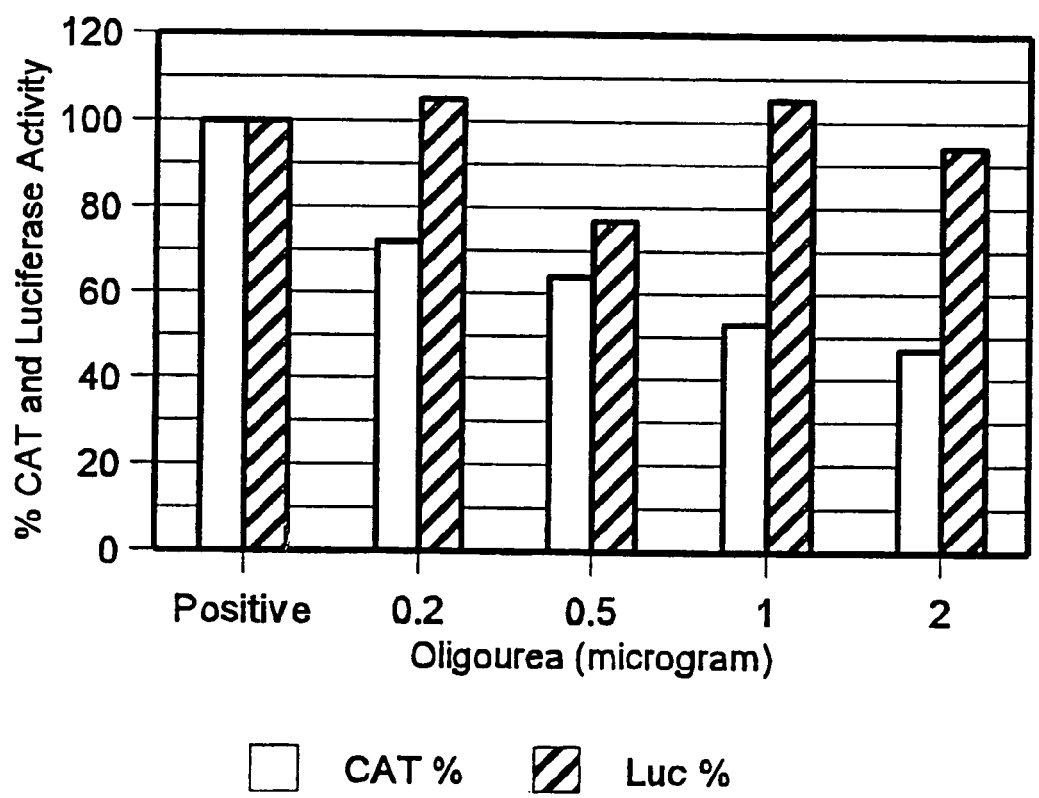
FIG. 4. Inhibition of Tat transactivation by the oligourea derivative in vivo. CAT activity expressed from the integrated HIV-1 LTR of HL3TI Cells with increasing amounts of oligourea is shown. Luciferase activity was a control experiment to monitor the transfection inhibition of pSV2Tat by the addition of oligourea. CAT and Luciferase activities were measured from multiple experiments and normalized to 100%. Control lane (labeled as positive) shows Tat transactivation in the absence of oligourea.

To probe the oligourea-RNA interactions and determine the proteolysis stability of oligourea, we synthesized TAR RNA containing 4-thioU at position 23 and performed photocrosslinking experiments as described earlier (FIG. 3).[5,7] Irradiation of the oligourea-RNA complex yields a new band with electrophoretic mobility less than that of the RNA (lane 4). Both the oligourea and UV (360 nm) irradiation are required for the formation of this crosslinked RNA-oligourea complex (see lanes 3 and 4). Since the crosslinked oligourea-RNA complex is stable to alkaline pH (9.5), high temperature (85° C.) and denaturing conditions (8M urea, 2% SDS), we conclude that a covalent bond is formed between TAR RNA and the oligourea during the crosslinking reaction.

To test the protease stability of the oligourea-RNA complexes, we subjected the oligourea-RNA crosslink products to very vigorous proteinase K digestion which showed that the complexes were completely stable and there were no signs of oligo urea degradation (lane 5 and 6). Under similar proteinase K treatment, Tat-TAR photocrosslink products resulted in a complete loss of RNA-protein crosslink and a gain in free RNA as observed by band intensities on the gel.[5]

These findings show that a small tat-derived oligourea binds TAR RNA specifically with high affinity and interacts in the major groove (4-thio groups at U23) of TAR RNA. Due to the difference in backbone structure, oligoureas may differ from peptides in hydrogen-bonding properties, lipophilicity, stability, and conformational flexibility. Moreover, oligoureas are resistant to proteinase K degradation. These characteristics of oligoureas may be useful in improving pharmacokinetic properties relative to peptides. RNA recognition by an oligourea provides a new approach for the design of drugs which will modulate RNA-protein interactions. Transfection enhancing agents could be utilized with drugs comprising the oligourea of the invention to ameliorate any problems associated with the transfection or uptake of the oligourea of the invention.

REFERENCES 1. (a) Geierstanger, B. H.; Mrksich, M.; Dervan, P. B.; Wemmer, D. E. *Science* 1994, 266, 646–50. (b) Gottesfeld, J. M.; Neely, L.; Trauger, J. W.; Baird, B. B.; Dervan, P. B. *Nature* 1997, 387, 202–205. (c) White, S.; Szewczyk, J.; Turner, J.; Baird, E. E.; Dervan, P. B. *Nature* 1998, 391, 468–471.
2. Tinoco, I., Jr.; Puglisi, J. D.; Wyatt, J. R. *Nucl. Acids & Mol. Biol.* 1990, 4, 205–226.
3. Jones, K. A.; Peterlin, B. M. *Annu. Rev. Biochem.* 1994, 63, 717–43.
4. (a) Puglisi, J. D.; Tan, R.; Calnan, B. J.; Frankel, A. D.; Williamson, J. *Science* 1992, 257, 76–80. (b) Aboul-ela, F.; Kam, J.; Varani, G. *J. Mol. Biol.* 1995, 253, 313–332.
5. (a) Wang, Z.; Rana, T. M. *J Am. Chem. Soc.* 1995, 117, 5438–5444. (b) Wang, z.; Rana, T. M. *Biochemistry* 1996, 35, 6491–6499. (c) Wang, Z.; Wang, x.; Rana, T. M. *J Biol. Chem.* 1996, 27], 16995–16998.
6. Huq, I.; Rana, T. M. Biochemistry 1997, 36, 12592–12599.
7. Wang, X.; Hug, I.; Rana, T. M. *J Am. Chem. Soc.* 1997, 119, 6444–6445.
8. (a) Cullen, B. R. *Microbiol. Rev.* 1992, 56, 375–394. (b) Gaynor, R. *AIDS* 1992, 6, 347–363. (c) Jeang, K.-T.; Berkhout, B.; Dropulic, B. *J Biol. Chem.* 1993, 268, 24940–24949.
9. (a) Calnan, B. J.; Biancalana, S.; Hudson, D.; Frankel, A. D. *Genes Dev.* 1991, 5, 201–210. (b) Weeks, K. M.; Crothers, D. M. *Cell* 1991, 66, 577–588. (c) Churcher, M. J.; Lamont, C.; Hamy, F.; Dingwall, C.; Green, S. M.; Lowe, A. D.; Butler, P. J. C.; Gait, M. J.; Karn, J. *J Mol. Biol.* 1993, 230, 90–110.
10. (a) Burgess, K.; Linthicum, D. S.; Shin, H. *Angew. Chem. Int. Ed. Engi.* 1995, 34, 907–909. (b) Burgess, K.; Ibarzo, J.; Linthicum, D. S.; Russell, D. H.; Shin, H.; Shitangkoon, A.; Totani, R.; Zhang, A. J. *J Am. Chem. Soc.* 1997, 119, 1556–1564.
11. Kim, J. M.; Bi, Y. Z.; Paikoff, S. J.; Schultz, P. G. *Tetrahedron Lett.* 1996, 37, 5305–5308.
12. Kick, B.; Bllman, J. *J Med. Chem.* 1995, 38, 1427–1430.

---

---

We claim:

1. A synthesized oligourea comprising the following structure:

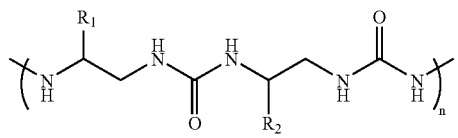

wherein n=3–50; and $R_1$ and $R_2$ are independently each amino acid side chains comprising the basic-arginine rich region of HIV-1 Tat protein.

2. A method of inhibiting the binding of Tat protein to Tar RNA comprising introducing the oligourea of claim 1 into a cellular environment in vitro wherein the inhibition is sought to occur.

3. The method of claim 2 wherein the cellular environment is one infected by the HIV-1.

4. The method of claim 3 wherein the oligourea of claim 1 binds to the TAR RNA of HIV-1, thereby limiting the binding of Tat to TAR RNA.

5. A composition comprising an oligourea, wherein the oligourea comprises the following structure:

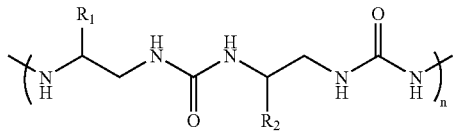

wherein n=3–50; and $R_1$ and $R_2$ are independently each amino acid side chains comprising the basic-arginine rich region of HIV-1 Tat protein.

6. The composition of claim 5, wherein the $R_1$ and $R_2$ amino acid side-chains correspond to SEQ ID NO: 1.

7. The composition of claim 5, wherein the $R_1$ and $R_2$ amino acid side-chains correspond to the SEQ ID NO: 1 with a L-Tyr amino acid at the carboxyl-terminus.

8. The oligourea of claim 1, wherein the $R_1$ and $R_2$ amino acid side chains correspond to SEQ ID NO:1.

9. The oligourea of claim 1, wherein the $R_1$ and $R_2$ amino acid side chains correspond to SEQ ID NO:1 with a L-Tyr amino acid at the carboxyl-terminus.

10. The oligourea of claim 1, wherein the $R_1$ and $R_2$ amino acid side chains correspond to SEQ ID NO:1 with a L-Tyr amino acid at the amino-terminus.

11. The oligourea of claim 1, wherein n is 5–30.

12. The oligourea of claim 1, wherein n is 8–25.

13. The composition of claim 5, wherein the $R_1$ and $R_2$ amino acid side chains correspond to SEQ ID NO:1 with a L-Tyr amino acid at the amino-terminus.

* * * * *

UNITED STATES PATENT AND TRADEMARK OFFICE
CERTIFICATE OF CORRECTION

| | |
|---|---|
| PATENT NO. | : 7,056,656 B1 |
| APPLICATION NO. | : 09/889982 |
| DATED | : June 6, 2006 |
| INVENTOR(S) | : Rana et al. |

It is certified that error appears in the above-identified patent and that said Letters Patent is hereby corrected as shown below:

On the cover page at (74) Attorney, Agent or Firm should read --Hoffmann & Baron, LLP--.

At column 5, line 30, the printed patent should read --In a more preferred embodiment, the patient...--.

Signed and Sealed this

Nineteenth Day of December, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Gly Arg Lys Lys Arg Arg Gln Arg Arg Arg
1               5                   10